United States Patent [19]

Schubart et al.

[11] 4,148,800

[45] Apr. 10, 1979

[54] PROCESS FOR THE PRODUCTION OF THIAZOLINE-2-THIONES

[75] Inventors: Rüdiger Schubart, Bergisch-Gladbach; Ulrich Eholzer, Cologne, both of Fed. Rep. of Germany

[73] Assignee: Bayer Aktiengesellschaft, Leverkusen, Fed. Rep. of Germany

[21] Appl. No.: 867,049

[22] Filed: Jan. 5, 1978

[30] Foreign Application Priority Data

Jan. 13, 1977 [DE] Fed. Rep. of Germany ....... 2701215

[51] Int. Cl.² .......................................... C07D 277/04
[52] U.S. Cl. ............................................. 260/306.7 R

[58] Field of Search ................................. 260/306.7 R

[56] References Cited

U.S. PATENT DOCUMENTS

| | | | |
|---|---|---|---|
| 2,860,962 | 11/1958 | Bluestone | 260/306.7 |
| 3,215,703 | 11/1965 | Sullivan et al. | 260/306.7 |
| 3,370,051 | 2/1968 | Sullivan et al. | 260/306.7 |

*Primary Examiner*—Nicholas S. Rizzo
*Attorney, Agent, or Firm*—Connolly and Hutz

[57] ABSTRACT

One-pot process for producing thiazoline-2-thiones by reacting corresponding aminoethanols with thionylchloride, heating the resulting product and reacting it subsequently with carbon disulphide.

4 Claims, No Drawings

PROCESS FOR THE PRODUCTION OF THIAZOLINE-2-THIONES

This invention relates to a process for the production of thiazoline-2-thiones which can be obtained in high yields.

In principle, this synthesis process is a multistage synthesis by the one-pot process which takes place in accordance with the following scheme:

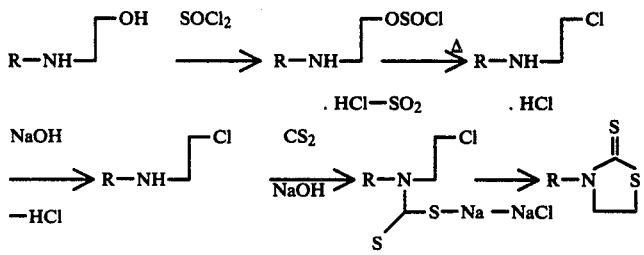

First of all, aminoethanols are reacted with thionyl chloride in an inert solvent at room temperature, optionally with cooling. The intermediate product formed gives off sulphur dioxide on gentle heating. To complete the reaction, the temperature is increased in stages to around 100° C., depending upon the evolution of sulphur dioxide. After the evolution of gas has stopped, the inert solvent may be concentrated by evaporation. The chloroethyl amine hydrochloride formed may be re-dissolved by adding water. However, it is also possible not to distill off the insert solvent, but instead to remove it by phase separation after the addition of water. In addition, it is also possible not to remove the inert solvent and to carry out the following reaction in the presence of two phases.

For the further reaction, the hydrochloride present in the aqueous phase is initially converted with a basic compound into the free "chloroethyl amine" which is then further reacted with carbon disulphide to form the "dithiocarbamic acid salt". This is followed by cyclisation to form the thiazoline-2-thione by the elimination of hydrogen chloride which has to be collected by the addition of another mole of alkali metal hydroxide or half a mole of aklkaline earth metal hydroxide, or even alkali or alkaline earth metal carbonate and also by tertiary amine.

In cases where tertiary amine is used, it is also possible to work entirely in the organic phase, i.e., in the absence of water.

It has been found to be best, for avoiding large quantities of effluent, to work with the highest possible concentration and to carry out the reactions of the N-chloroethyl amine hydrochloride with the above-mentioned bases in the presence of carbon disulphide. This avoids autocondensations of the chloroethyl amine and hence losses of yield.

The compounds are crystalline ($R_1 = CH_3$ or H) or liquid ($R = \geq C_2$; e.g., n-propyl, n-butyl, ethyl, 2-ethylhexyl). In the case of liquid products, isolation by phase separation does not involve any problems. Low-melting compounds, for example N-methylthiazoline-2-thione, can also be isolated in crystalline form. However, this necessitates drying in vacuo and grinding. It is more favourable, however, to bring the water/product mixture to the melting point of the product and to separate the thiazoline-2-thione by phase separation. The still moist melt is freed from residues of inert solvent and moisture in a thin-layer evaporator and subsequently converted on a scraper roller or on a crystallisation belt into the conveniently useable flake form commonly encountered in practice.

The yield is substantially quantitative. The effluent is substantially free from product and only contains alkali metal chloride.

Accordingly, the present invention provides a process for the production of thiazoline-2-thiones corresponding to the general formula (1) or (2):

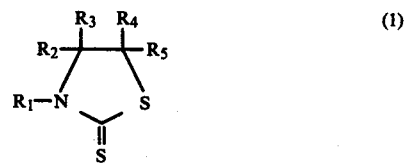
(1)

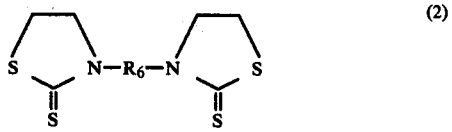
(2)

in which $R_1$ represents hydrogen or a straight-chain, saturated, unsaturated, branched or cyclic alkyl radical, which may optionally be interrupted by hetero atoms, or an aryl radical, these radicals optionally being substituted by mono- or di-alkylamino, alkoxy, alkylthio and/or halogen groups and, in the case of an aryl radical, an alkyl radical may additionally be present.

$R_2$ and $R_3$ may be the same or different and represent alkyl radicals or phenyl, the alkyl radicals optionally being attached to one another to form a 5-membered or 6-membered ring, $R_6$ represents an alkylene or phenylene group, wherein, in a one-pot process, corresponding aminoethanols or bis-(aminoethanols) are reacted with thionyl chloride in an inert solvent at temperatures of from 0° to 40° C., the product obtained is heated to temperatures of from 40° C. to 100° C., water is added after the evolution of gas has stopped, followed by reaction with carbon disulphide in the presence of basic compounds at temperatures of from 0° to 120° C.

The present invention also relates to new compounds corresponding to the formula:

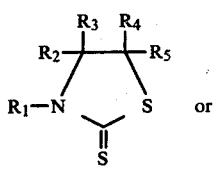

or

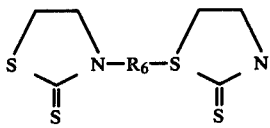

in which

R₁ represents an alkyl radical with 1 to 6 carbon atoms or a radical $R_7$-$X$-$R_8$, where $R_7$ is an alkyl radical with 1 to 8 carbon atoms, X is oxygen or sulphur and $R_8$ is an alkyl radical with 1 to 3 carbon atoms, or a radical $(R_7)_2$-N-$R_8$ where $R_7$ and $R_8$ are as already defined, or a cycloalkyl ring with 5 to 7 carbon atoms which may optionally be substituted by up to 4 methyl groups and which, in addition, may contain a hetero atom, such as nitrogen or oxygen, in the ring system, R₂ and R₃ represent hydrogen, R₄ represents phenyl, hydrogen, alkyl or vinyl, R₅ represents hydrogen or an alkyl radical with 1 to 6 carbon atoms, alkyl or vinyl and R₆ represents an alkylene radical with 2 to 6 carbon atoms.

Preferably, the reaction with thionyl chloride is carried out at 20° to 35° C., the evolution of gas at 60° to 70° C. and the reaction with carbon disulphide at 20° to 40° C.

The substituent R₁ preferably represents an optionally substituted alkyl radical containing from 1 to 18 carbon atoms and, with particular preference, from 1 to 8 carbon atoms. The following are examples of substituents for the alkyl radical: mono- or di-alkylamine, preferably with C₁-C₄-alkyl groups, alkoxy radicals with preferably C₁-C₈-alkyl, alkylthio radicals with preferably C₁-C₄-alkyl and halogen atoms, preferably chlorine.

If the aryl radical is substituted by an alkyl radical, the alkyl radicals in question are C₁-C₄-alkyl radicals.

The substituents R₂-R₅ are the same or different and preferably represent alkyl groups with 1 to 6 carbon atoms.

The substituent R₆ is preferably C₂-C₆-alkylene.

The following radicals are mentioned by way of example: ethyl, propyl, isopropyl, butyl, isobutyl, sec.-butyl, methyl, tert.-butyl, pentyl, isopentyl, sec.-pentyl, tert.-pentyl, hexyl, sec.-hexyl, tert.-hexyl, heptyl, octyl, 2-ethylhexyl, nonyl, decyl, undecyl, dodecyl, tridecyl, tetradecyl, hexadecyl, octadecyl, dimethylaminoethyl, dimethylaminopropyl, methoxyethyl, ethoxyethyl, isopropoxyethyl, propoxyethyl, methoxypropyl, ethoxypropyl, propoxypropyl, isopropoxypropyl, methylthioethyl, methylthiopropyl, ethylthiopropyl, ethylthioethyl, propylthioethyl, propylthiopropyl, dimethylaminomethyl, diethylaminomethyl, methoxymethyl, ethoxymethyl, propoxymethyl, isopropoxymethyl, butoxymethyl, butylthiomethyl, isopropylthiomethyl, chloroethyl, chloropropyl, cyclohexyl, cyclopentyl, cycloheptyl, cyclohexylmethyl, phenyl, 2-methylphenyl, 3-methylphenyl, 4-methylphenyl, 2,3-dimethylphenyl, 3,4-dimethylphenyl, 4-piperidinyl, 2,2,6,6-tetramethylpiperidinyl, morpholinyl, phenylene, ethylene, propylene, pentylene, butylene, hexylene, isopropenyl, phenylthioethyl, phenylthiopropyl, ethylhexyloxypropyl, diisobutyl and di-tert.-dodecyl.

The following compounds are mentioned by way of example: thiazoline-2-thione, N-methyl thiazoline-2-thione, N-ethyl thiazoline-2-thione, N-propyl thiazoline-2-thione, N-isopropyl thiazoline-2-thione, N-butyl thiazoline-2-thione, N-sec.-butyl thiazoline-2-thione, N-tert.-butyl thiazoline-2-thione, N-pentyl thiazoline-2-thione, N-sec.-pently thiazoline-2-thione, N-isopentyl thiazoline-2-thione, N-tert.-pentyl thiazoline-2-thione, N-isobutyl thiazoline-2-thione, N-hexyl thiazoline-2-thione, N-sec.-hexyl thiazoline-2-thione, N-isohexyl thiazoline-2-thione, N-tert.-hexyl thiazoline-2-thione, N-heptyl thiazoline-2-thione, N-isoheptyl thiasoline-2-thione, N-tert.-heptyl thiazoline-2-thione, N-octyl thiazoline-2-thione, N-iso-octyl thiazoline-2-thione, N-nonyl thiazoline-2-thione, N-decyl thiazoline-2-thione, N-undecyl thiazoline-2-thione, N-decyl thiazoline-2-thione, N-tridecyl thiazoline-2-thione, N-tetradecyl thiazoline-2-thione, N-pentadecyl thiazoline-2-thione, N-hexadecyl thiazoline-2-thione, N-heptadecyl thiazoline-2-thione, N-octadecyl thiazoline-2-thione, N-dimethylaminoethyl thiazoline-2-thione, N-diethylaminoethyl thiazoline-2-thione, N-dipropylaminoethyl thiazoline-2-thione, N-dimethylaminopropyl thiazoline-2-thione, N-diethylaminopropyl thiazoline-2-thione, N-dipropylaminopropyl thiazoline-2-thione, N-dimethylaminomethyl thiazoline-2-thione, N-methoxyethyl thiazoline-2-thione, N-ethoxyethyl thiazoline-2-thione, N-propoxyethyl thiazoline-2-thione, N-methoxypropyl thiazoline-2-thione, N-ethoxypropyl thiazoline-2-thione, N-propoxypropyl thiazoline-2-thione, N-diethylaminomethyl thiazoline-2-thione, N-methylthiomethyl thiazoline-2-thione, N-ethylthiomethyl thiazoline-2-thione, N-propylthiomethyl thiazoline-2-thione, N-methylthioethyl thiazoline-2-thione, N-ethylthioethyl thiazoline-2-thione, N-propylthioethyl thiazoline-2-thione, N-butylthioethyl thiazoline-2-thione, N-methylthiopropyl thiazoline-2-thione, N-ethylthiopropyl thiazoline-2-thione, N-propylthiopropyl thiazoline-2-thione, N-butylthiopropyl thiazoline-2-thione, N,N'-propylenebis-thiazoline-2-thione, N,N'-butylene-bis-thiazoline-2-thione, N,N'-pentylene-bis-thiazoline-2-thione, N,N'-hexylenebis-thiazoline-2-thione, N,N'-phenylene-bis-thiazoline-2-thione, N-phenylthioethyl thiazoline-2-thione, N-phenylthio-propyl thiazoline-2-thione, N-hydroxyethyl thiazoline-2-thione, N-hydroxypropyl thiazoline-2-thione, N-chloroethyl thiazoline-2-thione, N-chloropropyl thiazoline-2-thione, N-cyclohexyl thiazoline-2-thione, N-cyclopentyl thiazoline-2-thione, N-cycloheptyl thiazoline-2-thione, N-cyclohexylmethyl thiazoline-2-thione, N-phenyl thiazoline-2-thione, N-methylphenyl thiazoline-2-thione, N-methyl-4,5-dimethyl thiazoline-2-thione, N-methyl-4,4,5-trimethyl thiazoline-2-thione, N-methyl-4,5,5-trimethyl thiazoline- 2-thione, N-methyl-4,4-dimethyl thiazoline-2-thione, N-methyl,5,5-dimethyl thiazoline-2-thione, N-methyl-4,4,5,5-tetramethyl thiazoline-2-thione, N-ethyl-4,4,5,5-tetramethyl thiazoline-2-thione, N-ethyl-4,5-dimethyl thiazoline-2-thione, N-ethyl-4-methyl thiazoline-2-thione, N-ethyl-5-methyl thiazoline-2-thione, N-ethyl-4,4-dimethyl thiazoline-2-thione, N-ethyl-5,5-dimethyl thiazoline-2-thione, N-ethyl-4,5-diethyl thiazoline-2-thione, N-ethyl-4-ethyl thiazoline-2-thione, N-ethyl-5-ethyl thiazoline-2-thione, N-ethyl-4-phenyl thiazoline-2-thione, N-methyl-4-ethyl thiazoline-2-thione, N-methyl-5-ethyl thiazoline-2-thione, N-cyclohexyl-4,5-dimethyl thiazoline-2-thione, N-cyclohexyl-4,4-dimethylthiazoline-2-thione, N-cyclohexyl-5,5-dimethyl thiazoline-2-thione, N-cyclohexyl-5-ethyl thiazoline-2-thione, N-cyclohexyl-4-ethyl thiazoline-2-thione, N-phenyl-4,5-dimethyl thiazoline-2-thione, N-phenyl-5-ethyl thiazoline-2-thione, N-(4-piperidinyl)-thiazoline-2-thione, N-[4-(2,2,6,6-tetramethylpiperidinyl)]-thiazoline-2-thione, N-methyl isopropyl thiazoline-2-thione, N-phenyl-5-methyl thiazoline-2-thione, N-phenyl-4-phenyl thiazoline-2-thione, N-cyclohexyl-5-methyl thiazoline-2-thione, N-cyclohexyl-4-methyl thiazoline-2-thione, N-phenyl-5,5-dimethyl thiazoline-2-thione, N-phenyl-4,4-dimethyl thiazoline-2-thione, N-methyl-4,5-trimethylene thiazoline-2-thione, N-methyl-4,5-tetramethylene thiazoline-2-thione, N-methyl-4,5-pentamethylene thiazoline-2-thione, N-methyl-4,4,5,5-bis-trimethylene thiazoline-2-thione, N-methyl4,4,5,5-bis-tetramethylene thiazoline-2-thione, N-methyl-4-methyl thiazoline-2-thione, N-methyl-5-methyl thiazoline-2-thione, N-ethylhecyl thiazoline-2-thione, N-methyl-4-phenyl thiazoline-2-thione, N,N'-ethylene-bis-thiazoline-2-thione, N,N'-propylene-bis-thiazoline-2-thione, N-isopropyl-5-methyl thiazoline-2-thione, N-isopropyl-4-methyl thiazoline-2-thione, N-isopropyl-4,5-dimethyl thiazoline-2-thione, N-isopropyl-5,5-dimethyl thiazoline-2-thione, N-isopropyl-4,4-dimethyl thiazoline-2-thione, 3,4-trimethylene thiazoline-2-thione, 3,4-tetramethylene thiazoline-2-thione, 3,5-trimethylene thiazoline-2-thione, 3,5-tetramethylene thiazoline-2-thione, N-methyl-4-vinyl thiazoline-2-thione, N-methyl-5-vinyl thiazoline-2-thione.

According to the stoichiometric equation, 1 mole of thionyl chloride may be used per mole of starting material. In many cases, it is advantageous to use an excess of up to 10 mole percent of the chlorinating agent. It is particularly favourable to use an excess of from 3 to 6 mole percent. In order to facilitating working up of the end product, it is advisable to use no more than molar quantities of carbon disulphide. It is advantageous to use a slight deficit of up to about 5 mole percent.

Preferred basic compounds, which may be used both for forming the free "chloroethyl amine" and also for cyclisation to give the thiazoline-2-thione, are alkali or alkaline-earth metal oxides, hydroxides or carbonates and also tertiary amines, such as for example sodium hydroxide, potassium hydroxide, calcium hydroxide, strontium hydroxide, barium hydroxide, sodium carbonate, potassium carbonate, calcium carbonate, strontium carbonate and barium carbonate.

The compound is preferably used in molar quantitive ratios, although slight deviations are also possible.

The compounds produced in accordance with the invention may be used as vulcanisation accelerators for polychloroprene rubbers according to U.S. Pat. Nos. 3,215,703 and 3,215,704. In the following Examples the percentages are by weight:

EXAMPLE 1

300 g (4 moles) of methylaminoethanol are added dropwise while cooling to 600 ml of chlorobenzene and 505 g (approximately 5% excess) of thionyl chloride over a period of 1 to 1.5 hours at room temperature to 35° C. The mixture is then heated in stages of 10° C. (according to the intensity of the evolution of $SO_2$) to a temperature of 60° C. and, after the evolution of gas has stopped, is briefly heated up to 70° C. (over a period of 2 to 3 hours. After cooling, 0.8 liter of water is added, the mixture is briefly stirred until a clear solution has formed and the supernatant chlorobenzene phase is separated off. The aqueous solution is cooled to 10° to 15° C., 298 g (98%) of carbon disulphide are added and the mixture is reacted with concentrated sodium hydroxide solution over a period of 2 to 3 hours with stirring and cooling. The mixture is then stirred at pH 8 until there is no further change in the pH-value (which takes about 0.5 to 1 hour). The reaction mixture is then neutralised with a little acetic acid. Therefore, it is heated to 65°–70° C. The molten product (lower phase) is separated off in a preheated separation funnel, washed once with 100 ml of water heated to 70° C. and dried in vacuo. N-methyl thiazoline-2-thione melting at 69° to 70° C. is left behind in a yield of 511 g, corresponding to 96% of the theoretical yield.

EXAMPLE 2

In contrast to Example 1, the reaction was carried out without separating off the chlorobenzene. The end product is situated in the chlorobenzene phase. Concentration of the chlorobenzene solution by evaporation gives N-methyl thiazoline-2-thione in a yield of 99%.

EXAMPLE 3

In contrast to Example 1, the end product was not worked up in the melt. After stirring at pH 8, the N-methyl thiazoline-2-thione formed is filtered under suction, washed and dried in vacuo. Yield: 97%.

| Table of compounds produced in accordance with Example 1 | | | |
|---|---|---|---|
| Starting material | New synthesis product | Melting point °C. | Refractive index ($n_{20}$) |
| N-methylaminoethanol | N-methyl thiazoline-2-thione | 69–70 | |
| N-ethylaminoethanol | N-ethyl thiazoline-2-thione | | 1.6355 |
| N-propylaminoethanol | N-propyl thiazoline-2-thione | | 1.6120 |
| N-tert.-butylaminoethanol | N-tert.-butyl thiazoline-2-thione | 68–69 | |
| N-cyclohexylaminoethanol | N-cyclohexyl thiazoline-2-thione | 115–116 | |
| N-cyclohexyl-2-aminopropanol | N-cyclohexyl-5-methyl thiazoline-2-thione | 85–87 | |
| N-cyclohexyl-2-aminobutanol | N-cyclohexyl-5-ethyl thiazoline-2-thione | 74.5–76.5 | |
| N-isopropyl-2-aminobutanol | N-isopropyl-5-ethyl thiazoline-2-thione | 51–52 | |
| N-isopropylamino-1-phenylethanol | N-isopropyl-4-phenyl thiazoline-2-thione | 65.5–66.5 | |
| N-isopropylaminoethanol | N-isopropyl thiazoline-2-thione | 46–47 | |
| N-isopropyl-2-aminopropanol | N-isopropyl-5-methyl thiazoline-2-thione | 61–62 | |
| N-benzylaminoethanol | N-benzyl thiazoline-2-thione | 131–132 | |
| N-methyl-2-aminopropanol | N-methyl-5-methyl thiazoline-2- | | |

| Table of compounds produced in accordance with Example 1 | | | |
|---|---|---|---|
| Starting material | New synthesis product | Melting point °C. | Refractive index ($n_{20}$) |
| | thione | | 1.6272 |
| N-phenylaminoethanol | N-phenyl thiazoline-2-thione | 121–124 | |
| N-methyl-2-aminobutanol | N-methyl-5-ethyl thiazoline-2-thione | | 1.6059 |
| N-(hexyl-2-ethyl)-aminoethanol | N-(2-ethylhexyl)-thiazoline-2-thione | | 1.5617 |
| N-ethyl-2-aminobutanol | N-ethyl-5-ethylthiazoline-2-thione | | 1.5895 |
| aminobutanol | thiazoline-2-thione | 102–103 | |
| N-methylamino-1-phenylethanol | N-methyl-4-phenyl thiazoline-2-thione | 51–52 | |
| N-methoxypropylaminoethanol | N-methoxypropyl tiazoline-2-thione | | 1.5952 |
| N-ethoxypropylaminoethanol | N-ethoxypropyl thiazoline-2-thione | | 1.5747 |
| N-(2-ethylhexyloxypropyl)-amino ethanol | N-(2-ethylhexyloxypropyl)-thiazoline-2-thione | | 1.5332 |
| 2-aminopropanol | | 94–95 | |
| N-(diethylaminopropyl)-amino-ethanol | N-(diethylaminopropyl)-thiazoline-2-thione | | 1.5676 |
| N-methylthioethyl aminoethanol | N-methylthioethyl thiazoline-2-thione | | 1.6490 |
| N,N'-bis-hydroxyethyl ethylene diamine | N,N'-bis-(thiazoline-2-thione)-ethylene | 228–232 | |
| N,N'-bis-hydroxyethyl-1,2-propylene diamine | N,N'-bis-(thiazoline-2-thione)-1,2-propylene | 131–136 | |

We claim:

1. In a one-pot process for the production of thiazoline-2-thiones the improvement comprises the steps of
   (a) reacting an aminoethanol with thionyl chloride in an inert solvent at 0° to 40° C.,
   (b) heating the reaction product to 40° to 100° C. until evolution of SO₂ ceases, and
   (c) adding water and reacting the product from step b) with carbon disulfide in the presence of basic compounds at 0° to 120° C.

2. A process as claimed in claim 1, wherein the reaction with thionyl chloride is carried out at temperatures of from 20° to 35° C.

3. A process as claimed in claim 1, wherein the evolution of gas takes place at 60° to 70° C.

4. A process as claimed in claim 1, wherein the reaction with carbon disulphide is carried out at 20° to 40° C.